United States Patent
Hasebe et al.

(10) Patent No.: US 6,830,754 B2
(45) Date of Patent: *Dec. 14, 2004

(54) AMPHIPATIC LIPID DISPERSION

(75) Inventors: Keiko Hasebe, Wakayama (JP); Juri Sata, Wakayama (JP); Yasuhiro Doi, Wakayama (JP); Yoshinori Tamura, Wakayama (JP); Masaki Inoue, Wakayama (JP); Hiroshi Sonohara, Wakayama (JP)

(73) Assignee: Kao Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 473 days.

(21) Appl. No.: 09/468,777

(22) Filed: Dec. 21, 1999

(65) Prior Publication Data

US 2002/0058052 A1 May 16, 2002

(30) Foreign Application Priority Data

Dec. 25, 1998 (JP) ............................................ 10-370658

(51) Int. Cl.⁷ ............................ A61K 6/00; A61K 7/00; A61K 7/06; A61K 7/075; A61K 7/08
(52) U.S. Cl. .................. 424/401; 424/70.1; 424/70.21; 424/70.31; 424/78.03; 514/613; 514/666; 514/667; 514/669; 514/671; 514/880
(58) Field of Search .................. 424/401, 70.1, 424/70.21, 70.22, 70.31; 514/613, 666, 667, 669, 671

(56) References Cited

U.S. PATENT DOCUMENTS

| | | | | |
|---|---|---|---|---|
| 4,152,272 A | * | 5/1979 | Young | 252/8.8 |
| 5,306,488 A | * | 4/1994 | Vanlerberghe et al. | 424/71 |
| 5,368,857 A | * | 11/1994 | Corcoran et al. | 424/401 |
| 5,476,661 A | * | 12/1995 | Pillai et al. | 424/401 |
| 5,618,523 A | | 4/1997 | Zysman et al. | |
| 5,661,118 A | * | 8/1997 | Cauwet et al. | 510/126 |
| 5,679,357 A | * | 10/1997 | Dubief et al. | 424/401 |
| 5,688,752 A | * | 11/1997 | Turner | 510/159 |
| 5,700,456 A | * | 12/1997 | Dubief et al. | 424/70.17 |
| 5,773,611 A | | 6/1998 | Zysman et al. | |
| 5,851,541 A | * | 12/1998 | Corey et al. | 424/401 |
| 5,985,255 A | * | 11/1999 | Vanlerberghe et al. | 424/70.28 |

FOREIGN PATENT DOCUMENTS

| | | |
|---|---|---|
| EP | 0 487 958 | 6/1992 |
| JP | 64-9913 | 1/1989 |
| JP | 5-220383 | 8/1993 |
| JP | 6-502660 | 3/1994 |
| JP | 8-59443 | 3/1996 |
| WO | WO 93/02656 | 2/1993 |

OTHER PUBLICATIONS

Merriam–Webster's Colligiat Dictionary. 2002 Encyclopaedia Britannica, Inc.*

* cited by examiner

*Primary Examiner*—Sreeni Padmanabhan
*Assistant Examiner*—Lauren Q. Wells
(74) *Attorney, Agent, or Firm*—Oblon, Spivak, McClelland, Maier & Neustadt, P.C.

(57) ABSTRACT

Described in the present invention are a dispersion which comprises, as a dispersoid, (a) 5 to 40 wt. % of an amphipatic lipid containing, in the molecule thereof, at least one hydroxy and amide group, and (b) 2 to 55 wt. % of a surfactant in an aqueous medium; a washing-away type cosmetic composition comprising the dispersion; and a washing-away type cosmetic composition comprising (A) 0.01 to 10 wt. % of an amphipatic lipid which contains, in the molecule thereof, at least one hydroxy and amide group and having a melting point not less than 30° C. and (B) 5 to 95 wt. % of a surfactant. The dispersion according to the present invention is useful as a component of a washing-away type cosmetic composition having both an emulsion-like or pearl-lustrous appearance and low skin irritation. The washing-away type cosmetic composition according to the present invention has an emulsion-like or pearl-lustrous appearance and is mild to the skin owing to reduced adsorption, to the skin, of the surfactant contained in the composition.

11 Claims, No Drawings

AMPHIPATIC LIPID DISPERSION

BACKGROUND OF THE INVENTION

1. Field of the Invention

The present invention relates to a dispersion containing an amphipatic lipid as a dispersoid, a washing-away type cosmetic composition which comprises the amphipatic lipid, has an emulsion-like or pearl-lustrous appearance and has low skin irritation, and another washing-away type cosmetic composition which comprises an amphipatic lipid having a definite average particle size, has an emulsion-like or pearl-lustrous appearance and has low skin irritation.

2. Description of the Related Art

With a view to imparting good appearance to a washing-away type cosmetic composition such as body shampoo, hair shampoo, rinse or the like which is washed away after application to the skin or hair, a dispersion of an emulsifying agent or a pearling agent is conventionally employed for such a composition to impart it an emulsion-like or pearl-lustrous appearance.

Such a washing-away type cosmetic composition contains a surfactant, which sometimes causes dry skin or inflammation. Surfactants not so irritating to the skin are therefore being developed, but development of a novel low-irritating surfactant needs tremendous time and cost.

There are several attempts made to incorporate an amphipatic lipid such as ceramide in a washing-away type cosmetic composition, thereby protecting the skin or hair. Described specifically, reported are a hair cosmetic composition comprising an amide derivative, which is a substance analogous to ceramide (Japanese Patent Application Laid-Open No. 9913/1989); a hair cosmetic composition comprising a glycoceramide and a cationic surfactant (Japanese Patent Application 502660/1994); and a cleansing or treatment composition for hair or skin which comprises an anionic surfactant, amphoteric surfactant, cationic polymer and ceramide or glycoceramide (Japanese Patent Application Laid-Open No. 59443/1996). In the above-described cosmetic compositions, however, only a small amount (about 2 wt. % at the maximum) of a ceramide can be incorporated stably because it is solid at room temperature. On the other hand, if the ceramide is incorporated in the cosmetic composition after it is dissolved in another medium and then emulsified, it does not exhibit sufficient effects.

An object of the present invention is therefore to provide a washing-away type cosmetic composition which can sufficiently exhibit properties of an amphipatic lipid which is in the solid form at room temperature and a dispersion employed for it.

SUMMARY OF THE INVENTION

In one aspect of the present invention, there are thus provided a dispersion comprising, in an aqueous medium, the following components (a) and (b):

(a) 5 to 40 wt. % of, as a dispersoid, an amphipatic lipid having, in the molecule thereof, at least one hydroxy and amide group; and (b) 2 to 55 wt. % of a surfactant; and a washing-away type cosmetic composition comprising the dispersion.

In another aspect of the present invention, there is also provided a washing-away type cosmetic composition comprising the following components (A) and (B):

(A) 0.01 to 10 wt. % of an amphipatic lipid having an average particle size of 0.5 to 150 μm and having, in the molecule of the amphipatic lipid, at least one hydroxy and amide group; and (B) 5 to 95 wt. % of a surfactant.

The dispersion according to the present invention has, as a dispersoid, a solid-particulate amphipatic lipid dispersed in an aqueous medium. It is useful as a component for a washing-away type cosmetic composition having both good emulsion-like or pearl-lustrous appearance and having low skin irritation. The washing-away type cosmetic composition according to the present invention has, as described above, a good emulsion-like or pearl-lustrous appearance and in addition, has low skin irritation because the amount of the surfactant, which is contained in the composition, adsorbed to the skin is small.

DETAILED DESCRIPTION OF THE PREFERRED EMBODIMENTS

The term "an amphipatic lipid which has, in the molecule of thereof, at least one hydroxy and amide group" means a natural ceramide or a synthetic ceramide, or a substance analogous thereto (pseudo-ceramide) available by the synthesis or the like of the natural or synthetic ceramide, which is in the solid form at room temperature (25° C.). Examples of the amphipatic lipid include "Ceramide H03" (trade name, product of Sederma S. A.), Ceramide II (trade name, product of Sederma S. A.), "Questamide H" (trade name, product of Quest International), "Ceramide TIC-001" (trade name, product of Takasago International Corp.), and "Sofcare Ceramide SL-E" (trade name; product of Kao Corp.). The amphipatic lipid is preferred to have a melting point not less than 30° C., more preferably not less than 40° C. in consideration of the stability of the dispersion or the like formed using it. Particularly preferred examples of the ceramide analogous substance available by synthesis include amide derivatives represented by the below-described formula (1) including the above-exemplified Sofcare Ceramide SL-E.

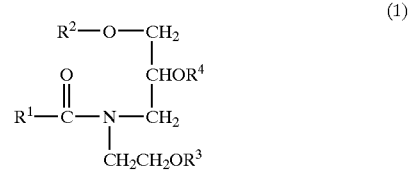

(1)

wherein $R_1$ and $R_2$ are the same or different and each independently represents a linear or branched, saturated or unsaturated $C_{7-39}$ hydrocarbon group which may be substituted by at least one hydroxyl group, and $R_3$ and $R_4$ are the same or different and each independently represents a hydrogen atom, a phosphate salt residue, a sulfate salt residue or a saccharide residue, with the proviso that at least one hydroxyl group is contained in the molecule.

In the formula (1), preferred as $R_1$ are linear or branched, saturated or unsaturated $C_{9-25}$ hydrocarbon groups, preferred as $R_2$ are linear or branched, saturated or unsaturated, $C_{10-26}$ hydrocarbon groups and preferred as $R_3$ or $R_4$ is a hydrogen atom.

The preparation process of the above-described amide derivative (1) is described specifically in Japanese Patent Application Laid-Open No. 228048/1987, Japanese Patent Application Laid-Open No. 216852/1988 and the like.

As the amphipatic lipid serving as the component (a), those exemplified above can be used either singly or in combination. In the dispersion of the present invention, it is incorporated in an amount of 5 to 40 wt. %, preferably 10 to 30 wt. %.

As the surfactant serving as the component (b) of the dispersion of the present invention, at least one surfactant selected from nonionic surfactants, anionic surfactants, amphoteric surfactants and the like ordinarily employed for cosmetics can be used. Among them, examples of the nonionic surfactant include alkyl polyglycosides, polyoxyalkylene alkyl or alkenyl ethers, polyoxyalkylene sorbitan fatty acid esters, sorbitan fatty acid esters, polyoxyalkylene sorbitol fatty acid esters, polyoxyalkylene glycerin fatty acid esters, polyglycerin fatty acid esters, fatty acid monoglycerides, polyethylene glycol fatty acid esters and fatty acid alkanol amides. Examples of the anionic surfactant include polyoxyalkylene alkyl ether acetic acids or salts thereof, N-acylamino acid salts, polyoxyalkylene alkyl ether sulfate salts, polyoxyalkylene alkyl ether phosphate salts, alkyl phosphate salts, N-acylmethyl taurine salts, alkyl sulfosuccinate salts, polyoxyalkylene alkylsulfosuccinate salts and fatty acid salts. Examples of amphoteric surfactant include alkylaminoacetate betaines, alkylamine oxides, alkylamidopropyl betaines, alkylhydroxysulfobetaines and amidoamino acids (imidazoline-type betaines).

Among them, preferred are nonionic surfactants and polyoxyethylene alkyl ether acetic acids or salts thereof. As the nonionic surfactant, that selected from alkyl polyglycosides, polyoxyalkylene alkyl or alkenyl ethers, polyoxyalkylene sorbitan fatty acid esters and sorbitan fatty acid esters is preferred.

Particularly preferred examples of the nonionic surfactant include alkyl polyglycosides, for example, those in which the alkyl group has 8 to 14 carbon atoms and the condensation degree of glucose is 1 to 2; polyoxyalkylene alkyl or alkenyl ethers, for example, those in which the alkyl or alkenyl group has 8 to 18 carbon atoms and the number of moles of the added ethylene oxide is 4 to 25, preferably 4 to 15 on average; polyoxyalkylene sorbitan fatty acid esters in which the fatty acid has 8 to 20 carbon atoms and the number of moles of the added ethylene oxide is 5 to 25 on average; and sorbitan fatty acid esters, for example, monoesters of a $C_{8-20}$ fatty acid. Examples of the polyoxyethylene alkyl ether acetic acid and salt thereof include polyoxyethylene alkyl ether-acetic acids which have 8 to 20 carbon atoms and in which the number of moles of the added ethylene oxide is 3 to 15 on average and alkali metal salts thereof. In other words, polyoxyethylene alkyl ether acetic acids can be used as they are without neutralization or after neutralized as needed. The further addition of a cationic surfactant can heighten adsorption of an amphipatic lipid to the skin or hair.

As the component (b), the above-exemplified surfactants may be used either singly or in combination. It is added in an amount of 2 to 55 wt. %, preferably 5 to 40 wt. % to the dispersion of the present invention.

Here, the amphipatic lipid (a) and surfactant (b) are added at an (a)/(b) weight ratio of 90/10 to 25/75, preferably 80/20 to 30/70, particularly preferably 70/30 to 40/60.

The dispersion according to the present invention can be prepared, for example, by heating a mixture of the amphipatic lipid (a), the surfactant (b) and water to the melting point of the amphipatic lipid or higher (melting point to melting point+about 10° C.), thereby fusing it while stirring; and after the resulting mixture becomes uniform, cooling it while stirring to crystallize the component (a).

The particle size of the component (a) can be controlled by adjusting the kind or amount of the surfactant, cooling rate, stirring speed or the like. The component (a) is preferred to have an average particle size, as measured by the method described later, of 0.5 to 150 μm, more preferably 1 to 150 μm, particularly preferably 1 to 80 μm. To the dispersion of the present invention, it is possible to add ethylene glycol distearate, ethylene glycol monostearate, another pearling agent, emulsifying agent, pH regulator, antiseptic or the like before or after the above-described heating, fusing or cooling.

The dispersion of the present invention thus obtained has an emulsion-like or pearl-lustrous appearance so that incorporation of it in a washing-away cosmetic composition makes it possible to impart the cosmetic composition with an emulsion-like or pearl-lustrous appearance, and in addition, to reduce the amount of the surfactant, which is contained in the washing-away cosmetic composition, adsorbed to the skin, thereby reducing the skin irritation caused by the surfactant.

Examples of the washing-away type cosmetic composition of the present invention include hair cosmetic compositions such as shampoo and rinse, facial ones such as face wash and facial pack and those for systemic application such as massage oil, cream and the like and body shampoo. The dispersion according to the present invention is particularly useful as a component of a cleansing agent containing a surfactant as a base, such as systemic cleansing agent, hand and finger cleansing agent and facial wash.

The amount of the invention dispersion to be added to a washing-away type cosmetic composition may be adjusted as needed, depending on the kind of the cosmetic composition or concentration of the dispersion. Amphipatic lipid concentrations ranging from 0.01 to 10 wt. %, particularly, 0.1 to 5 wt. % are usually preferred.

Upon preparation of a washing-away type cosmetic composition by using the dispersion of the present invention, it is preferred to premix components of the cosmetic composition other than the dispersion and then mix the resulting mixture with the dispersion at not more than 50° C. Such a procedure makes it possible to stably incorporate the amphipatic lipid, which has been contained in the dispersion, in the cosmetic composition.

As the surfactant to be used for the washing-away type cosmetic composition prepared using the dispersion, those exemplified later as the component (B) can be mentioned as examples. The amount of the surfactant is, based on the amount of the washing-away type cosmetic composition, 5 to 95 wt. %, preferably 10 to 50 wt. %, more preferably 10 to 35 wt. % in terms of the total amount of the surfactants used for the preparation of the dispersion and the washing-away type cosmetic composition.

As the amphipatic lipid (A) to be used for the washing-away type cosmetic composition of the present invention, amide derivatives (1) are particularly preferred similar to the case of the component (a) in the above-described dispersion. They may be used either singly or in combination, but an average particle size of it (them) is preferably 0.5 to 150 μm, more preferably 1 to 150 μm, still more preferably 1 to 80 μm, particularly preferably 1 to 50 μm from the viewpoints of the irritation reducing effects and stability in the washing-away type cosmetic composition. The term "average particle size" as used herein means an arithmetically calculated average length, in a straight line, of the longest portions of 30 particles selected optionally from a micrograph of the washing-away type cosmetic composition taken by an optical microscope under a transmitted light. The amphipatic lipid (A) is added in an amount of 0.01 to 10 wt. %, preferably 0.1 to 5 wt. % to the washing-away type cosmetic composition of the present invention.

As the surfactant (B), those exemplified above as the component (b) of the dispersion and those ordinarily added to a washing-away type cosmetic composition for the purpose of cleansing or softening of the hair can be mentioned. Preferred examples include alkyl polyglycosides, fatty acid alkanol amides, amidoamino acid surfactants (imidazoline betaines), alkylaminoacetate betaines, alkylamine oxides, alkylamidopropyl betaines, alkylhydroxysulfobetaines and anionic surfactants, with alkyl polyglycosides, amidoamino acid surfactants (imidazoline betaines) and anionic surfactants being more preferred. Among the anionic surfactants, preferred are polyoxyalkylene alkyl ether sulfates, for example, those containing an alkyl group having 12 to 18 carbon atoms and having 2 to 4 moles on average of added ethylene oxide; fatty acid salts, for example, those containing a fatty acid having 12 to 18 carbon atoms; alkyl phosphates, for example, those containing an alkyl group having 12 to 18 carbon atoms; polyoxyalkylene alkyl ether phosphates, for example, those containing an alkyl group having 12 to 18 carbon atoms and having 1 to 5 moles on average of added ethylene oxide; polyoxyalkylene alkyl ether acetates, for example, those containing an alkyl group having 12 to 18 carbon atoms and having 3 to 12 moles on average of added ethylene oxide; acylated amino acid salts, for example, those containing an acyl group having 12 to 18 carbon atoms and being a derivative of alanine, sarcosine, glycine or glutamic acid; alkyl sulfate salts, alkyl sulfosuccinate salts and polyoxyethylene alkylsulfosuccinate salts each containing an alkyl group having 12 to 18 carbon atoms; and acylated isethionate salts and N-acylmethyltaurine salts each containing an acyl group having 12 to 18 carbon atoms. Preferred examples of the salt include salts soluble in water such as alkali metal salts and alkanolamine salts. The surfactant serving as the component (B) is added in an amount of 5 to 95 wt. %, preferably 10 to 50 wt. %, more preferably 10 to 35 wt. % based on the washing-away cosmetic composition of the present invention.

To the washing-away cosmetic composition of the present invention, it is possible to add optionally an oil such as higher alcohol, lanolin, squalane, hydrocarbon or silicone; a cationized polymer such as cationized cellulose, cationized guar gum or "Mercoat 550" (product of Merck & Co., Inc); a water-soluble macromolecule such as methyl cellulose, hydroxyethyl cellulose, carboxyvinyl polymer or polysaccharide (xanthan gum, etc.); a viscosity regulator or solubilizing assistant such as polyoxyalkylene sorbitan ester, polyoxyethylene fatty acid ester, ethanol, glycerin or sorbitol; a chelating agent such as ethylenediamine tetraacetate (EDTA) or phosphate salt; an antiseptic such as methyl paraben or butyl paraben; a nutrient such as vitamin or precursor thereof; an animal or vegetable extract such as lecithin or gelatin, or derivative thereof; a fine-particulate polymer such as nylon or polyethylene; an anti-inflammatory agent such as dipotassium glycyrrhizinate or allantoin; a bactericide or anti-dandruff agent such as benzalkonium chloride, benzalkonium cetylphosphate ("SANISOL P", trade name; product of Kao Corporation), triclosan, trichlorocarban, octopirox or zinc pyrithione; an antioxidant such as dibutylhydroxytoluene; an ultraviolet absorber; a pH regulator; a colorant; a perfume; and/or the like.

Upon preparation of the washing-away cosmetic composition of the present invention, an amphipatic lipid may be used as is or in the form of a dispersion, and preferably used in the form of a dispersion. When the amphipatic lipid is used as is, it is preferred to dissolve the amphipatic lipid together with the other components of the cosmetic composition by heating or to disperse them uniformly, and then cool the whole mixed system to crystallize the amphipatic lipid.

The washing-away type cosmetic composition of the present invention can be converted into any dosage form such as solid, paste or liquid.

EXAMPLES

Example 1

After 15 parts by weight of an amphipatic lipid [being represented by the formula (1) wherein $R_1=C_{15}H_{31}$, $R_2=C_{16}H_{33}$, $R^3=H$ and $R^4=H$ and having a melting point of 74 to 76° C.], 25 parts by weight of "MYDOL 10" [trade name, product of Kao Corporation; effective ingredient: 40 wt. %; decyl polyglycoside (condensation degree: 1 to 1.35)] and 60 parts by weight of water were heated to 80 to 85° C., they were cooled while stirring, whereby the amphipatic lipid was crystallized. Cooling was continued further to room temperature while stirring, whereby a dispersion of the amphipatic lipid was prepared.

The resulting dispersion had a pearl-lustrous appearance and the amphipatic lipid particles in the dispersion were needle crystals having an average particle size of 15.1 μm.

Examples 2 to 7

In each of Examples 2 to 7, the dispersion of an amphipatic lipid as shown in Table 1 having a pearl-lustrous appearance was prepared as a target product.

TABLE 1

| | | Examples | | | | | | |
|---|---|---|---|---|---|---|---|---|
| | | 2 | 3 | 4 | 5 | 6 | 7 | 8 |
| (a) Amphipatic lipid | Formula (1); $R^1 = C_{17}H_{35}$, $R^2 = C_{14}H_{29}$, $R^3 = H$, $R^4 = H$ (melting point: 78 to 80° C.) | 5.0 | | | | | | |
| | Formula (1); $R^1 = C_{15}H_{31}$, $R^2 = C_{16}H_{33}$, $R^3 = H$, $R^4 = H$ (melting point: 74 to 76° C.) | 15.0 | 20.0 | | 18.0 | 15.0 | 20.0 | 20.0 |
| | Formula (1); $R^1 = C_{13}H_{27}$, $R^2 = C_{18}H_{37}$, $R^3 = H$, $R^4 = H$ (melting point: 68 to 70° C.) | | | 28.0 | | | | |
| | Formula (1); $R^1 = C_9H_{19}$, $R^2 = C_{16}H_{33}$, $R^3 = H$, $R^4 = H$ (melting point: 53 to 57° C.) | | 3.0 | | | 3.0 | | |
| | Ceramide II[*1] (melting point: 85 to 100° C.) | | | | 2.0 | | | |
| | Ceramide H03[*1] (melting point: 97 to 100° C.) | | | | | 3.0 | | |
| (b) Surfactant | MYDOL 10 | 37.5 | | | | | | 37.5 |
| | MYDOL 12[*2] | | | 50.0 | | | | |
| | EMULGEN 106[*3] | | 15.0 | | | 13.0 | | |
| | RHEODOL TW-0120[*4] | | | | 12.0 | | | |
| | KAO AKYPO RLM-45[*5] | | | | | | 8.0 | |
| | KAO AKYPO RLM-100[*6] | | | | | | 15.0 | |
| | AMPHITOL 55AB[*7] | | | | | | | 10.0 |
| Water | | balance | balance | balance | balance | balance | balance | balance |
| Appearance | | pearl | pearl | pearl | pearl | pearl | pearl | pearl |
| Average particle size (μm) | | 12.0 | 5.1 | 23.6 | 19.2 | 10.5 | 15.0 | 8.4 |

[*1]: SEDERMA
[*2]: Kao, lauryl polyglycoside, condensation degree: 1 to 1.35, effective ingredient: 40%
[*3]: Kao, polyoxyethylene (5) lauryl ether
[*4]: Kao, polyoxyethylene (20) sorbitan monooleate
[*5]: Kao, polyoxyethylene (4.5) lauryl ether acetic acid, effective ingredient: 92%
[*6]: Kao, polyoxyethylene (10) lauryl ether acetic acid, effective ingredient: 89%
[*7]: Kao, coconut oil fatty acid amidopropyl betaine, effective ingredient: 30%

Example 9

Systemic Cleansing Agent 1

A pearl-lustrous systemic cleansing agent 1 having the below-described composition was prepared in a conventional manner. The amphipatic lipid was however added later at 40° C. in the form of a pearl-lustrous dispersion (Example 1) which had been crystallized in advance.

| | (parts by weight) |
|---|---|
| Laurylphosphoric acid | 13.0 |
| Triethanolamine (89%) | 9.4 |
| Lauroyl diethanolamide | 1.0 |
| Lauroyl amidopropyl betaine | 1.5 |
| Lauryl dimethylamine oxide | 1.5 |
| Amphipatic lipid (Example 1) | 7.0*1 |
| Water | Balance |
| Total | 100.0 |

*1 Amount added as the pearl-lustrous dispersion of Example 1 (which will be applied equally hereinafter) Example 10: Systemic cleansing agent 2

A pearl-lustrous systemic cleansing agent 2 having the below-described composition was prepared in a conventional manner. The amphipatic lipid was however added later at 40° C. in the form of a pearl-lustrous dispersion (Example 2) which had been crystallized in advance.

| | (parts by weight) |
|---|---|
| Polyoxyethylene coco-ether sulfate sodium salt (EO = 3) | 16.0 |
| Lauroyl diethanolamide | 1.0 |
| Coconut oil fatty acid amide propyl betaine | 3.0 |
| Sodium coco-amphoacetate | 1.5 |
| Amphipatic lipid (Example 2) | 7.5 |
| Water | Balance |
| Total | 100.0 |

Test 1: Amount of Surfactant Adsorbed

Male and female subjects, each three, were asked to use the systemic cleansing agent 1 of Example 9 for 1 week and from their brachial part, the stratum corneum was collected by the tape stripping method. The tape used for collection was cut into pieces, followed by extraction with methanol. The amount of lauryl phosphoric acid, which was a main surfactant of the systemic cleansing agent, adsorbed to the skin was determined by subjecting the extract to liquid chromatography.

For comparison, a similar test was conducted on a comparative systemic cleansing agent having a similar composition to the systemic cleansing agent 1 of Example 9 except that the amphipatic lipid was omitted and the residue was balanced with water.

Results are shown in Table 2.

TABLE 2

| | | Amount of lauryl phosphoric acid in the stratum corneum (μg/cm²-skin) | |
|---|---|---|---|
| | | Systemic cleansing agent 1 | Comparative systemic cleansing agent 1 |
| Subjects | A | 3.2 | 8.8 |
| | B | 4.5 | 11.3 |
| | C | 3.9 | 11.0 |
| | D | 2.6 | 7.8 |
| | E | 2.7 | 7.2 |
| | F | 4.8 | 10.4 |
| Average | | 3.6 | 9.4 |

From the above results, it has been found that compared with the comparative product, the invention product can significantly reduce the adsorption amount of the surfactant to the skin.

Test 2: Test on Effects for Alleviating Itch or Dry Skin

Men and women troubled with itch or dry skin in winter season when the air was dry were sampled as subjects. With five men and five women as one group, itch and dry skin after application of the systemic cleansing agent of Example 9 or 10 for 1 month were ranked in accordance with the below-described standards. The ranking was conducted by self-declaration system.

For comparison, a similar test was conducted on comparative systemic cleansing agents 1 and 2 which had similar compositions to the systemic cleansing agents of Examples 9 and 10, respectively except that the amphipatic lipid was omitted and the residue was balanced with water.

(Ranking Standards)

The symptom disappeared completely (improved): 0

The symptom almost disappeared (almost improved): 1

The symptom disappeared a little (slightly improved): 2

The symptom showed no change: 3

The symptom became severer (exacerbated): 4

(Results)

The results are shown in Table 3 as an average point of 10 subjects.

TABLE 3

| | Systemic cleansing agents of the present invention | | Comparative systemic cleansing agents | |
|---|---|---|---|---|
| | 1 | 2 | 1 | 2 |
| Itch | 1.0 | 1.4 | 2.6 | 2.8 |
| Dry skin | 0.9 | 0.9 | 1.8 | 2.1 |

As is apparent from the above-described results, itch and dry skin were significantly alleviated by the cleansing agents according to the present invention compared with the comparative ones.

Test 3: Test on Foamability

As samples, 5 wt. % solutions, each 100 mL, of the systemic cleansing agent 1 and comparative cleansing agent 1 were used, respectively. After each of the samples was diluted with hard water having hardness of 4 degrees and 0.5 wt. % of lanolin was added to the diluted solution, an amount of foams (mL) was measured at 40° C. by the reversal agitation method (Oil Chemistry, 22(4), 211(1973)). Measurements were conducted in 10 seconds after stirring for 30 seconds and in 30 seconds after stirring for 5 minutes. The results are shown in Table 4.

TABLE 4

| | | Systemic cleansing agent 1 | Comparative systemic cleansing agent 1 |
|---|---|---|---|
| Foamability | 10 sec after stirring for 30 sec | 215 | 205 |
| | 30 sec after stirring for 5 min | 385 | 380 |

As is apparent from the above results, the addition of the amphipatic lipid dispersion according to the present invention did not deteriorate the foamability of the cleansing agent.

Example 11

Face Wash 1

A pearl-lustrous face wash 1 having the below-described composition was prepared in a conventional manner. Upon preparation, however, the amphipatic lipid was added later at 40° C. in the form of a pearl-lustrous dispersion crystallized in advance (Example 3).

| | (parts by weight) |
|---|---|
| Stearic acid | 20.0 |
| Myristic acid | 12.0 |
| Lauric acid | 4.0 |
| Potassium hydroxide | 6.5 |
| Lauroyl amidopropyl betaine | 3.0 |
| Glycerin | 4.0 |
| Polyethylene glycol 6000 | 5.0 |
| Propylene glycol | 10.0 |
| Amphipatic lipid (Example 3) | 2.2 |
| Water | Balance |
| Total | 100.0 |

Example 12

Hand and Finger Cleansing Agent 1

A pearl-lustrous hand and finger cleansing agent 1 having the below-described composition was prepared in a conventional manner. Upon preparation, however, the amphipatic lipid was added later at 40° C. in the form of a pearl-lustrous dispersion (Example 1) crystallized in advance.

| | (parts by weight) |
|---|---|
| MYDOL 10 | 30.0 |
| Glycerin | 3.0 |
| RHEODOL TW-IS399C[*1] | 0.5 |
| Benzalkonium chloride | 0.8 |
| EDTA · 2Na | 0.3 |
| Amphipatic lipid (Example 1) | 10.0 |
| Water | Balance |
| Total | 100 |

[*1]polyoxyethylene sorbitan fatty acid ester (Kao Corp)

Example 13

Systemic Cleansing Agent 3

A pearl-lustrous systemic cleansing agent 3 having the below-described composition was prepared in a conventional manner. Upon preparation, however, the amphipatic lipid was added later at 40° C. in the form of a pearl-lustrous dispersion (Example 4) crystallized in advance.

|  | (parts by weight) |
| --- | --- |
| Sodium polyoxyethylene (4.5) lauryl ether acetate | 6.0 |
| Sodium polyoxyethylene (10) lauryl ether acetate | 5.0 |
| MYDOL 10 | 10.0 |
| Coconut oil fatty acid amidopropyl betaine | 3.0 |
| Polyoxyethylene (2) lauroyl monoethanolamide | 1.0 |
| Cationized cellulose | 0.1 |
| Glycerin | 3.0 |
| Amphipatic lipid (Example 4) | 7.0 |
| Water | Balance |
| Total | 100.0 |

Example 14

Systemic Cleansing agent 4 (Deodorant Type)

A deodorant-type pearl-lustrous systemic cleansing agent 4 having the below-described composition was prepared in a conventional manner. Upon preparation, however, the amphipatic lipid was added later at 40° C. in the form of a pearl-lustrous dispersion crystallized in advance (Example 1).

|  | (parts by weight) |
| --- | --- |
| Sodium polyoxyethylene (4.5) lauryl ether acetate | 5.0 |
| Sodium polyoxyethylene (10) lauryl ether acetate | 6.0 |
| MYDOL 10 | 5.0 |
| Lauroyl amidopropyl betaine | 2.0 |
| Lauroyl diethanolamide | 2.0 |
| Sorbitol | 1.0 |
| Dipotassium glycyrrhizinate | 0.1 |
| Triclosan | 0.2 |
| Amphipatic lipid (Example 1) | 5.0 |
| Water | Balance |
| Total | 100.0 |

Example 15

Systemic Cleansing Agent 5

A pearl-lustrous systemic cleansing agent 5 having the below-described composition was prepared in a conventional manner. Upon preparation, however, the amphipatic lipid was added later at 40° C. in the form of a pearl-lustrous dispersion crystallized in advance (Example 8).

|  | (parts by weight) |
| --- | --- |
| Lauroyl-β-alanine | 15.0 |
| Triethanolamine (89%) | 13.0 |
| Lauroyl amidopropyl betaine | 1.5 |
| Lauroyl diethanolamide | 1.5 |
| 1,3-Butanediol | 2.0 |
| Amphipatic lipid (Example 8) | 5.0 |
| Water | Balance |
| Total | 100 |

Example 16

Systemic Cleansing Agent 6

A pearl-lustrous systemic cleansing agent 6 having the below-described composition was prepared in a conventional manner. Upon preparation, however, the amphipatic lipid was added later at 35° C. in the form of a pearl-lustrous dispersion (Example 2) crystallized in advance after confirmation of the crystallization of ethylene glycol distearate.

|  | (parts by weight) |
| --- | --- |
| Potassium N-coconut oil fatty acid acyl-L-glutamate | 12.0 |
| Coconut oil fatty acid monoethanolamide | 2.0 |
| Lauroyl amidopropylbetaine | 1.5 |
| Glycerin | 3.0 |
| Ethylene glycol distearate | 1.0 |
| Amphipatic lipid (Example 2) | 4.0 |
| Water | Balance |
| Total | 100.0 |

The washing-away type cosmetic compositions obtained in Examples 9 to 16 were found to have a pearl-lustrous appearance, be free from irritation upon cleansing, have excellent touch feeling upon rinsing or drying and be mild to the skin even after daily or frequent use.

Japanese Patent Application No. 10-370658, filed on Dec. 25, 1998, is incorporated herein by reference in its entirety.

What is claimed is:

1. A dispersion comprising:
   (a) 5 to 40 wt. % of an amphipathic lipid having, in the molecule thereof, at least one hydroxy group and at least one amide group;
   (b) 2 to 55 wt. % of a surfactant; and
   (c) an aqueous medium,
   wherein said ampbipathic lipid has an average particle size of 0.5 to 150 μm and is dispersed in said surfactant and aqueous medium.

2. The dispersion of claim 1, wherein said surfactant (b) is selected from the group consisting of a nomonic surfactant, an anionic surfactant, an amphoteric surfactant and a mixture thereof.

3. The dispersion of claim 2, wherein said nonionic surfactant is selected from the group consisting of a alkyl polyglycoside, a polyoxyalkylene alkyl ether, a polyoxyalkylene alkenyl ether, a polyoxyalkylene sorbitan fatty acid ester, a sorbitan fatty acid ester and a mixture thereof.

4. The dispersion of claim 1, wherein a component (a)/component (b) weight ratio ranges from 90/10 to 25/75.

5. The dispersion of claim 1, wherein component (a) is a substance pseudo-ceramide.

6. The dispersion of claim 5, wherein the pseudo-ceramide is an amide derivative represented by the formula (1)

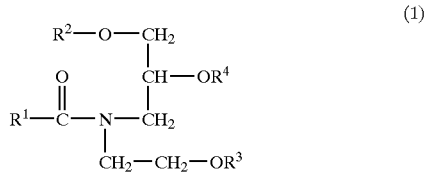

wherein $R^1$ and $R^2$ are the same or different and each independently represents a linear or branched, saturated or unsaturated hydrocarbon group which may be substituted by at least one hydroxyl group, and $R^3$ and $R^4$ are the same or different and each independently represents a hydrogen atom, a phosphate salt residue, a sulfate salt residue or a saccharide residue, with the proviso that at least one hydroxyl group is contained in the molecule.

7. A washing-away type cosmetic composition which is washed away after application to the skin or hair, which comprises the dispersion of any one of claims 1 to 3.

8. The dispersion of claim 1, wherein the dispersion is prepared by heating the component (a), the component (b) and water to a temperature not less than the melting point of the component (a), thereby fusing them; and cooling to crystallize the component (a).

9. A washing-away type cosmetic composition which is washed away after application to the skin or hair comprising:

(A) 0.01 to 10 wt. % of an amphipathic lipid having an average particle size of 0.5 to 150 μm as a solid particulate and having in the molecule thereof, at least one hydroxy group and at least one amide group; and (b) 5 to 95 wt. % of a surfactant.

10. A process for preparing a dispersion as claimed in any one of claims 1 to 3, which comprises heating the component (a), the component (b) and water to a temperature not less than the melting point of the component (a), thereby fusing them; and cooling to crystallize the component (a).

11. A process for preparing a washing-away type cosmetic composition which is washed away after application to the skin or hair, which comprises mixing the dispersion of any one of claims 1 to 3 with the components of the cosmetic composition other than the dispersion, at not more than 50° C.

* * * * *

UNITED STATES PATENT AND TRADEMARK OFFICE
CERTIFICATE OF CORRECTION

PATENT NO. : 6,830,754 B2
DATED : December 14, 2004
INVENTOR(S) : Keiko Hasebe et al.

It is certified that error appears in the above-identified patent and that said Letters Patent is hereby corrected as shown below:

<u>Title page</u>
Item [54], Title, "AMPHIPATIC LIPID DISPERSION", should read
-- AMPHIPATHIC LIPID DISPERSION --;
Item [57], ABSTRACT,
Lines 2 and 8, "amphipatic" should read -- amphipathic --.

<u>Column 1,</u>
Lines 8, 9, 12, 30, 54 and 62, "amphipatic" should read -- amphipathic --.

<u>Column 2,</u>
Lines 4, 6, 26, 32 and 39, "amphipatic" should read -- amphipathic --.

<u>Column 3,</u>
Lines 7 and 62, "amphipatic" should read -- amphipathic --.

<u>Column 4,</u>
Lines 1, 5, 7 and 55, "amphipatic" should read -- amphipathic --;
Line 46, "Amphipatic" should read -- Amphipathic --.

<u>Column 5,</u>
Lines 1 and 16, "amphipatic" should read -- amphipathic --.

<u>Column 6,</u>
Lines 25, 27, 28, 31, 44, 51, 54, 59 and 65, "amphipatic" should read -- amphipathic --.

<u>Column 7,</u>
TABLE 1 and Line 56, "Amphipatic" should read -- Amphipathic --;
Lines 45 and 65, "amphipatic" should read -- amphipathic --.

<u>Column 8,</u>
Line 48, "Amphipatic" should read -- Amphipathic --;
Line 66, "amphipatic" should read -- amphipathic --.

<u>Column 9,</u>
Line 32, "amphipatic" should read -- amphipathic --.

<u>Column 10,</u>
Lines 14, 24 and 50, "amphipatic" should read -- amphipathic --;
Lines 37 and 62, "Amphipatic" should read -- Amphipathic --.

UNITED STATES PATENT AND TRADEMARK OFFICE
CERTIFICATE OF CORRECTION

PATENT NO. : 6,830,754 B2
DATED : December 14, 2004
INVENTOR(S) : Keiko Hasebe et al.

It is certified that error appears in the above-identified patent and that said Letters Patent is hereby corrected as shown below:

Column 11,
Lines 7, 37 and 65, "amphipatic" should read -- amphipathic --;
Lines 24 and 53, "Amphipatic" should read -- Amphipathic --.

Column 12,
Lines 9 and 35, "Amphipatic" should read -- Amphipathic --;
Lines 20 and 55, "amphipatic" should read -- amphipathic --.

Column 13,
Line 19, "byat least" should read -- by at least --.

Signed and Sealed this

Twenty-second Day of March, 2005

JON W. DUDAS
*Director of the United States Patent and Trademark Office*